(12) United States Patent
Carr

(10) Patent No.: US 10,551,334 B1
(45) Date of Patent: Feb. 4, 2020

(54) IMPEDANCE SPECTROMETER WITH METAMATERIAL RADIATIVE FILTER

(71) Applicant: William N. Carr, Cary, NC (US)

(72) Inventor: William N. Carr, Cary, NC (US)

( * ) Notice: Subject to any disclaimer, the term of this patent is extended or adjusted under 35 U.S.C. 154(b) by 0 days.

(21) Appl. No.: 16/059,237

(22) Filed: Aug. 9, 2018

(51) Int. Cl.
   *G01N 27/02* (2006.01)
(52) U.S. Cl.
   CPC ................... *G01N 27/026* (2013.01)
(58) Field of Classification Search
   CPC ...... G01N 22/00; G01N 22/04; G01N 27/026; G01R 29/0814; G01R 29/0878; G01R 31/002
   See application file for complete search history.

(56) References Cited

U.S. PATENT DOCUMENTS

| | | | | | |
|---|---|---|---|---|---|
| 3,694,737 | A * | 9/1972 | Busker | ................... | G01N 22/04 324/640 |
| 3,715,667 | A * | 2/1973 | Nicolson | ................ | G01N 22/02 324/637 |
| 5,187,443 | A * | 2/1993 | Bereskin | .............. | G01R 1/0408 324/632 |
| 5,500,599 | A * | 3/1996 | Stange | ................... | G01N 22/00 324/632 |
| 6,839,035 | B1 * | 1/2005 | Addonisio | ......... | G06K 7/10178 340/572.1 |
| 7,315,173 | B2 * | 1/2008 | Funato | ............... | G01R 29/0814 324/452 |
| 7,336,230 | B2 * | 2/2008 | Lee | .................... | G01R 29/0828 324/627 |
| 8,542,122 | B2 * | 9/2013 | Goodnow | .......... | A61B 5/14532 340/572.1 |
| 9,460,320 | B2 * | 10/2016 | Ieki | ...................... | G06K 7/0008 |
| 2005/0073321 | A1 * | 4/2005 | Kohler | .................. | G01N 22/04 324/640 |
| 2007/0146138 | A1 * | 6/2007 | Phipps | ................. | G06K 7/0008 340/572.7 |
| 2007/0262869 | A1 * | 11/2007 | Young | ................ | G06K 7/10336 340/572.7 |
| 2008/0303717 | A1 * | 12/2008 | Durban | .................... | G01S 1/44 342/371 |

(Continued)

*Primary Examiner* — Christopher P McAndrew

(57) ABSTRACT

A system and method for sensing the wave impedance of a material using an RF power source with a sensor structure comprised of a metamaterial radiative filter (MRF). The wave impedance is specified or monitored by processing a differential RF signal level with an impedance calculator. The differential RF signal level is obtained from a reference source signal and a response signal. RF field-coupling of the RF source with the material effects the response signal level. In embodiments, the spectrometer is physically configured for noninvasive and invasive measurements. In embodiments, the material is sensed when shielded by RF-opaque media. In embodiments, wherein the MRF has a fixed response characteristic, the dielectric constant may be obtained with a sensing structure comprised of two transponders and a single RF frequency. In embodiments wherein the MRF has a fixed response characteristic, both the dielectric constant and the loss tangent may be obtained using three transponders and a single RF frequency. In embodiments wherein the MRF is tuned with programmed control, both the dielectric constant and the loss tangent may be obtained using two transponders and a single RF frequency.

20 Claims, 10 Drawing Sheets

(56) References Cited

U.S. PATENT DOCUMENTS

| | | | | |
|---|---|---|---|---|
| 2010/0066386 A1* | 3/2010 | Dos Santos | ............ | G01N 22/04 |
| | | | | 324/640 |
| 2010/0161004 A1* | 6/2010 | Najafi | .................. | A61N 1/3787 |
| | | | | 607/60 |
| 2010/0231407 A1* | 9/2010 | Carr | .................. | G06K 19/0723 |
| | | | | 340/691.1 |
| 2010/0271188 A1* | 10/2010 | Nysen | .................. | G01S 13/755 |
| | | | | 340/10.41 |
| 2012/0001730 A1* | 1/2012 | Potyrailo | ........... | G06K 7/10009 |
| | | | | 340/10.1 |
| 2012/0004851 A1* | 1/2012 | Potyrailo | ........... | G01N 33/0073 |
| | | | | 702/19 |
| 2012/0190310 A1* | 7/2012 | Ieki | ...................... | G06K 7/0008 |
| | | | | 455/73 |
| 2012/0256733 A1* | 10/2012 | Carr | .................. | G06K 19/0723 |
| | | | | 340/10.51 |
| 2012/0286935 A1* | 11/2012 | Huang | .................. | G01D 21/00 |
| | | | | 340/10.1 |
| 2013/0109305 A1* | 5/2013 | Savoj | .................. | G06K 7/0008 |
| | | | | 455/41.1 |
| 2014/0182363 A1* | 7/2014 | Potyrailo | ............. | G01N 27/026 |
| | | | | 73/64.53 |
| 2014/0224989 A1* | 8/2014 | Long | ..................... | G02F 1/0126 |
| | | | | 250/338.4 |

\* cited by examiner

800

US 10,551,334 B1

IMPEDANCE SPECTROMETER WITH METAMATERIAL RADIATIVE FILTER

STATEMENT OF RELATED CASES

This application is a continuation-in-part of U.S. patent application Ser. No. 15/507,215 currently allowed for issuance. The underlying concepts, but not necessarily the language, of the following cases are incorporated by reference:

(1) U.S. provisional application No. 62/043,376;
(2) U.S. provisional application No. 62/106,805;
(3) U.S. provisional application No. 62/210,888;
(4) U.S. provisional application No. 62/710,699.

If there are any contradictions or inconsistencies in language between this application and one or more of the cases that have been incorporated by reference that might affect the interpretation of the claims in this case, the claims in the case should be interpreted to be consistent with the language in this case.

This case claims benefit of the following provisional applications:

(1) U.S. provisional application No. 62/043,376;
(2) U.S. provisional application No. 62/106,805;
(3) U.S. provisional application No. 62/210,888;
(4) U.S. provisional application No. 62/710,699.

FIELD OF THE INVENTION

The present invention relates to wireless sensors in general, and, more particularly, to wireless sensors based on metamaterial technology.

BACKGROUND OF THE INVENTION

Instruments for determining the wave impedance of a material have been developed using many different sensing technologies that comprise separate components operating with different electromagnetic modalities. Related developments, including antennas and RFID tags, have been developed.

A planar loop antenna with a balun has been developed within a communication transceiver in U.S. Pat. No. 6,593,886. A communication link is disclosed as attenuated by a material.

An annular ring induction-type antenna is disclosed in U.S. Pat. No. 6,992,630, comprised of a plurality of circular rings operational within a communications system. The antenna is driven through an inner magnetically-coupled feed ring acting as a non-resonant coupler.

A prior art example of an antenna coupled into an adjacent medium is disclosed in U.S. Pat. No. 9,916,528. This wireless sensor determines a signal strength of radio-frequency energy emitted by an RFID tag wherein a signal strength is affected by the frozen or thawed state of a material disposed proximally with the tag. The sensing structure is an RFID tag.

In other prior art related to measurement of wave impedance of a material, a semi-passive transponder is disclosed in U.S. Patent Application 2017/0237466. This transponder is powered by RF energy harvesting. Energy harvesting is implemented via a resonant voltage multiplication circuit. A voltage multiplication circuit permits harvesting charge in nano- and micro-Joule increments to provide a transponder voltage higher than would otherwise be possible without the multiplier. RF energy is converted to a DC-level and stored over time to provide accumulated energy adequate to power full operation of the transponder.

There is a need for an impedance spectrometer sensing wave impedance of a material providing features of increased miniaturization, increased sensitivity and accuracy, increased tolerance to RF blocking environments, extended range and sensing for an increased number of material types.

SUMMARY OF THE INVENTION

The present invention provides an impedance spectrometer for sensing the RF wave impedance of a material, the spectrometer comprising a metamaterial radiative filter (MRF) and generally with a plurality of transponders. A particular advantage for using an MRF is the resulting structure is much smaller than traditional designs which involve separate physical components for providing field-coupling with a material, an RF filter, and a communications antenna.

Sensing operations of the present invention comprise a differential level which is processed to specify or monitor the wave impedance of a material. In some embodiments, differential levels are independent of the physical separation between the interrogator and the sensing structure, providing a unique advantage in applications.

The impedance calculator calculates either or both components of the wave impedance of a material. This calculation is based on a differential level further based on a source signal level and a response signal level. A means and method for determining RF wave impedance components of a material is disclosed. In some embodiments, the spectrometer includes:

an interrogator comprised of an RF power source, a communications and sensing controller, and a broadband first RF antenna, wherein the controller communicates with one or more transponders using a unique digital code with each transponder;

a sensing structure comprised of a metamaterial radiative filter (MRF) disposed within or proximal to the material, the MRF providing a selective RF filter and a wireless field-coupler, wherein the MRF, in response to RF power received from the interrogator, generates at least one or more of an electric, magnetic or electromagnetic field-coupling to the material, and the response of the MRF is effected by the wave impedance of the material;

a first transponder for determining a source signal level for RF power sourced from the interrogator, a second transponder for determining a response signal level effected by the MRF field-coupling of the RF power sourced from the interrogator, and an impedance calculator for specifying or monitoring the wave impedance of the material based on the source signal level and one or more response signal levels.

In embodiments, the sensing structure is comprised of the MRF a second physical transponder, and in other embodiments the MRF itself provides the second transponder function.

The second transponder determines one or more response signal levels. The one or more response signal levels are generated as backscatter signals to the interrogator or measured by the second transponder. During each sensing operation, the impedance calculator calculates a differential level based on the difference between a source signal level and a response signal level.

In a first sensing operation, the impedance calculator typically calculates the imaginary component X of the material based on a first differential level obtained at single frequency, the single frequency being different from the resonant frequency of the MRF. The dielectric constant of the material is directly related to the imaginary component X.

In second sensing operations, the impedance calculator determines the resonant frequency of the MRF and calculates a resonance differential level for the resonant frequency. The impedance calculator next calculates the real component R of the wave impedance based on the resonance differential level and the first differential level. The real component R of the material wave impedance is a unique function of the resonant differential response level and the first differential level. The real component R for a material of interest can be specified using calibrations based on a known material or monitored without calibrations. Based on calibrations using first and second sensing operations, the impedance calculator calculates the loss tangent $\delta=X/R$ of the material.

In some embodiments, a third sensing operation is implemented to obtain a differential signal using a third transponder and without an MRF. A response differential is obtained effected by attenuation of the RF signal over an extended path between a third transponder and the interrogator antenna. The third transponder generates a backscatter signal to the interrogator using a broadband antenna not effected by the imaginary part (dielectric constant) of the material. A third differential level is based on a source signal level and the backscatter response signal level at the interrogator. The impedance calculator specifies the real part R and the loss tangent of material impedance based on calibrations obtained with the first differential level and the third differential level.

In embodiments, wherein the MRF has a fixed response characteristic, the dielectric constant may be obtained with a sensing structure comprised of a single transponder and a single RF frequency. In embodiments wherein the MRF has a fixed response characteristic, both the dielectric constant and the loss tangent may be obtained with a sensing structure comprised of a single transponder using multiple RF frequencies. In an embodiment wherein the MRF is tuned with programmed control, both the dielectric constant and the loss tangent may be obtained with a sensing structure comprised of a single transponder using a single RF frequency.

Some embodiments of the present invention the MRF is embedded in the material to be tested. In other embodiments, the MRF is disposed in close proximity to the material and the wave impedance determination is noninvasive. In both cases, the field-coupling between the MRF and the material affects the response signal level.

Next the operational basics involving the MRF are presented. The MRF can be characterized by its resonant frequency and its quality factor. The resonant frequency of the MRF is strongly affected by the real part of the exposed material wave impedance. This response is illustrated in the exemplary simulation of FIG. 1A depicting the response of a selected MRF filter, field-coupled to a material. The MRF response is indicated by the filter return loss ratio $S_{11}$ of an MRF and is shown as a function of frequency and with the imaginary part X of the material as a parameter. The parameter curves 101 show the resonance frequency $f_o$ 102 of the MRF shifting to lower frequencies as the imaginary component X of the wave impedance increases. We note that the response of the MRF within a range of frequencies above resonance, such as $f_o$ 102, the response is uniquely related to the imaginary part of material wave impedance based on measurement of filter return loss ratio $S_{11}$.

Another uniqueness is illustrated in the exemplary simulation of FIG. 1B showing the filter return loss ratio $S_{11}$ of a selected MRF filter over a frequency range and field-coupled to a material having a uniform imaginary wave impedance component. This response is shown for several values of material loss tangent $\delta=R/X$. The resonant frequency of the MRF in this illustration is $f_{r2}$ 104. We note here that the MRF response measured within a frequency range $f_r$ 105 removed from the resonant frequency $f_{r2}$ is independent of the loss tangent $\delta$ for a (random) material. Further, the MRF response is strongly effected by the loss tangent $\delta$ at resonance frequency $f_{r2}$ 104.

A protocol for sensing operations is indicated by the simulations of FIG. 1. The protocol comprises three steps: Step 1: Determine a first response at first frequency $f_{r1}$ 103 wherein the imaginary part X of the wave impedance is uniquely specified or monitored. Step 2: Determine a second response at the MRF resonant frequency $f_{r2}$ strongly affected by the real part R of the wave impedance. Step 3: Determine the loss tangent $\delta=X/R$ based on steps 1 and 2.

The RF source is provided by the interrogator and its level is determined by a first transponder. In embodiments, the response signal level is a backscattered signal generated within the sensing structure and determined by one or more passive or semi-passive second transponders. In some embodiments, the response signal is measured at a transponder.

In embodiments, a range extender, connected between a first transponder and a broadband antenna, is at least partially embedded within a material that blocks RF communication. The range extender is comprised of a transmission line configured with or without connected baluns.

In embodiments, the interrogator provides an RF source of a single frequency, and in other embodiments, the RF source is sequenced through multiple RF frequencies.

Relating to embodiments, wherein the sensing structure is not tuned and wherein the sensing structure is comprised of only two transponders, the impedance calculator can calculate the real part of complex impedance of the material from measurements of differential signal levels obtained with sensing operations at a single frequency. In embodiments comprising a first and second transponder, the impedance calculator can calculate both the real part and the imaginary part of the complex impedance of the material from measurements of the differential signal levels obtained with sensing operations at multiple frequencies. In embodiments based on three transponders, the impedance calculator can calculate the real and imaginary part of the complex impedance of the material based on sensing operations using a single RF frequency.

In some embodiments, the sensing structure is tuned. In these embodiments, the sensing structure is tuned by the second transponder and sensing operations comprise a single RF source frequency. In these embodiments, both the real and imaginary wave impedance components are measured or monitored. In these embodiments, a tuned resonant element TRE in the form of a resonant LC tank circuit, not field-coupled with the material, is added in series or shunt with the MRF stripline connection. The resonant frequency of the TRE is determined by a varacter diode connected as capacitance C in the LC tank circuit of the TRE. The TRE provides a narrowband filter with passband or stopband determined by the varacter diode capacitance. Typically, the second transponder controls the capacitance C with a programmed voltage. In these tuned embodiments, the cross-correlation response of the TRE and the MRF provides a narrowband response for backscatter from the sensing structure. In this embodiment, the tuning of the TRE is controlled by the interrogator and communicated to transponder $T_2$ by wireless or wired means. The impedance calculator processes differential signal levels using a multivariate analysis to determine both the real and imaginary components of the material wave impedance. In these embodiments, wherein sensing structure is tuned and comprised of one or two transponders, both the real and imaginary components of material wave impedance are determined using a single RF frequency.

Figure 1A:
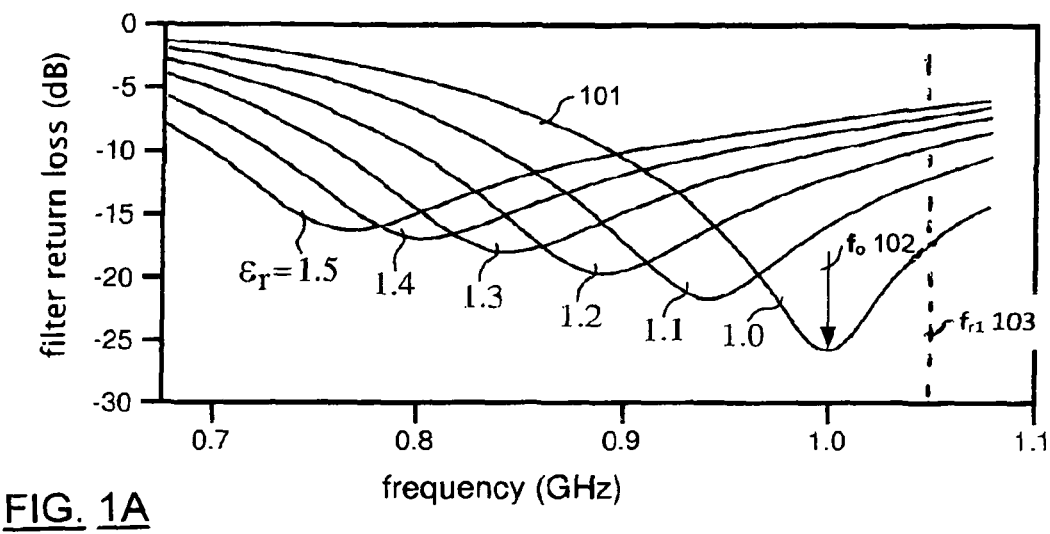
FIGS. 1A and 1B are graphs of filter signal loss ratio $S_{11}$ for a resonant circuit as a function of frequency.

The impedance calculator is part of the interrogator although the calculator function is not explicitly indicated in drawings.

DETAIL DESCRIPTION

Definitions

The following terms are explicitly defined for use in this disclosure and the appended claims:

"determines" referring to a signal level, means effecting or measuring a signal level.

"specifying" or "measuring" means providing a definite value for a signal level or a wave impedance component.

"monitoring" referring to a signal level or wave impedance component, means providing a relative value for a wave impedance implying a continued monitoring over time.

"sensing operation" means a spectrometer operation wherein a first source signal level and a response signal level are obtained to provide a differential signal level.

"wave impedance" or "bulk impedance" means the material permittivity $Z=R-jX$ comprising a real R and an imaginary X component. At the time of writing this disclosure, a relevant discussion of wave impedance is the Wikipedia entry: http://en.wikipedia.org/wiki/Wave_impedance.

"interrogator" means a device providing an RF power source and wireless or wired control for a sensing structure.

"transmitting" and "generating" means creation of an RF signal that is sourced directly from the interrogator or by backscattering of an incident RF signal at a transponder.

"impedance calculator" means the part of the interrogator that calculates the differential level and wave impedance of the material.

"transponder" means an RF device wherein a transfer characteristic is affected by an RF source signal.

"active transponder" means a transponder powered by an integral power source or through a databus connection.

"passive transponder" means a transponder powered only with energy harvested from a received RF signal.

"semi-passive transponder" means a transponder powered at least partially by energy sources other than the received RF signal.

"sensing structure" means a structure affected by the wave impedance of a material, wherein the structure is comprised of a metamaterial radiative filter (MRF).

"metamaterial radiative filter (MRF)" means a metamaterial sensor operational with at least one of negative permittivity or negative permeability providing both field couplings and a multi-port RF filter, the filter having an electrical transfer characteristic affected by the wave impedance of an exposed material and the RF frequency.

"tuned resonant element (TRE)" means a high-Q resonant tank circuit with LC elements in a series or parallel connection used to tune the sensing structure.

"ring resonator" means a resonant structural component of an MRF comprised of one or more of various structures including split rings, spiral rings and fractile variations thereof.

"range extender" means a component in embodiments comprised of a transmission line disposed at least partially within an RF-opaque material and terminated separately with a broadband antenna at a first port and a sensing structure at a second port.

"permittivity" means the real and imaginary components of the wave impedance of a material.

MRF STRUCTURES

The MRF structure in this invention is typically selected to provide maximum field-coupling into a material and wherein the filter return loss ratio $S_{11}$ has maximum frequency dispersion over the frequency range of interest. In all cases the MRF is a metamaterial operated in a frequency range wherein the electric permittivity and/or the magnetic permeability is negative. MRF structures providing a bianisotropic electromagnetic response are generally preferred for their higher radiation efficiency although other structures are used in some embodiments. In some embodiments, the MRF provides both an RF communications antenna for transmission through the material in addition to field-coupling to the material.

An increased frequency dispersion for the S-parameters near the MRF resonant frequency provides an increased incremental response signal with changing real part of the wave impedance of the material. This desired increased dispersion is obtained in embodiments at an RF frequency either lower than or higher than the resonance frequency of the MRF. In preferred embodiments, the MRF is comprised of a 2-dimensional, printed structure on a substrate comprised of one or more of flexible PET, FR-4, and other materials having low loss at the RF interrogator frequency. The MRF is generally field-coupled to a material of interest by an axial magnetic field or by means of an electric field applied in the orthogonal direction to the symmetry plane. Preferred structures for the MTF include an SRR, coupled spiral, and fractile variations thereof. The MRF is connected via a balanced and/or unbalanced stripline with one or more transponders within the sensing structure.

Figure 2A:
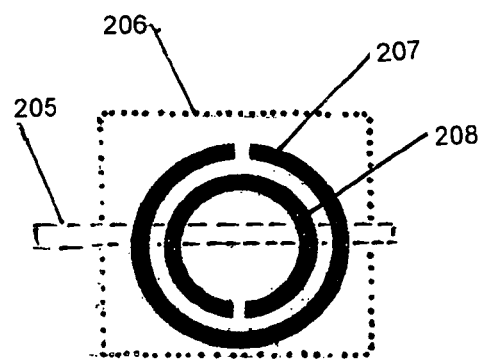
FIGS. 2A and 2B depict plan views of exemplary SRF structures coupled with balanced stripline in accordance with the present teachings.

FIG. 2A depicts a plan view of an MRF comprised of balanced transmission line field-coupled with an SRR. In a typical implementation, the stripline wires 205 and 210 are disposed on the topside of a low loss substrate, and the MRF is disposed on the reverse side. The outer ring 207 and the inner ring 208 of the SRR are framed within an area 206 surrounded by a ground plane metal film on the reverse side of the substrate. Both the stripline and MRF are typically created by subtractive lithographic patterning of the substrate obtained by processing metal films on both sides of the substrate.

Figure 2B:
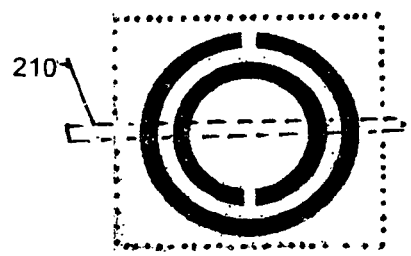
Figure 2B:
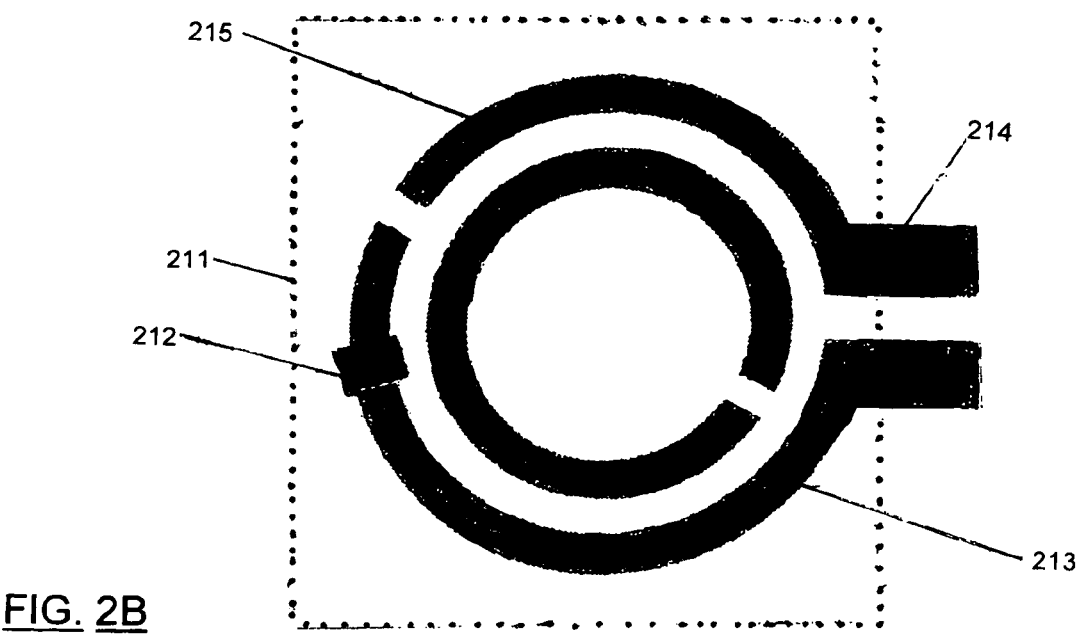

FIG. 2B depicts a plan view of an MRF wherein a balanced transmission line 214 is directly connected to the outer rings 213, 215 of an SRR. Transponder $T_2$ is disposed at an appropriate impedance point in a serial connection with the outer ring 213. The MRF is lithographically created from the topside metal film of the substrate. Backside metal is also removed from an area underneath the MRF to increase field-coupling of the MRF with the material of interest. In some embodiments, the MRF provides a second antenna, field-coupled with the first antenna of the interrogator. This MRF embodiment can be adapted to provide both a coupling with the material and the second transponder function.

Figure 3A:
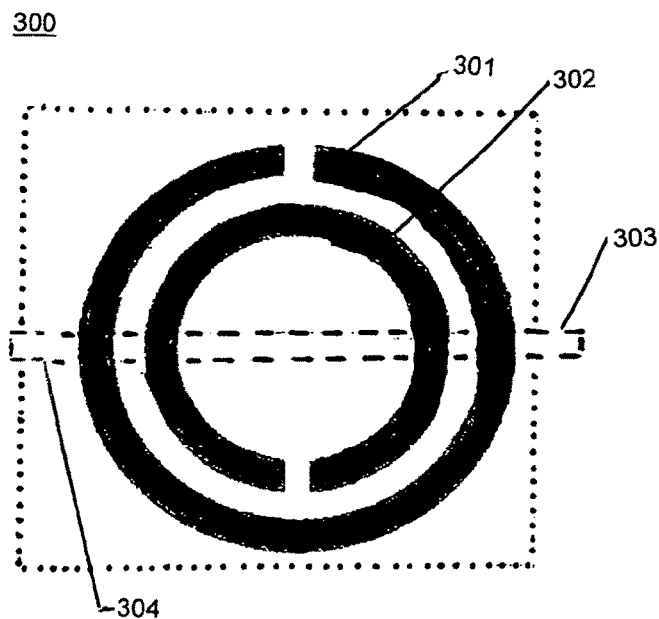
FIGS. 3A, 3B and 3C depict plan views of exemplary SRF structures coupled with unbalanced stripline in accordance with the present teachings.
Figure 3B:
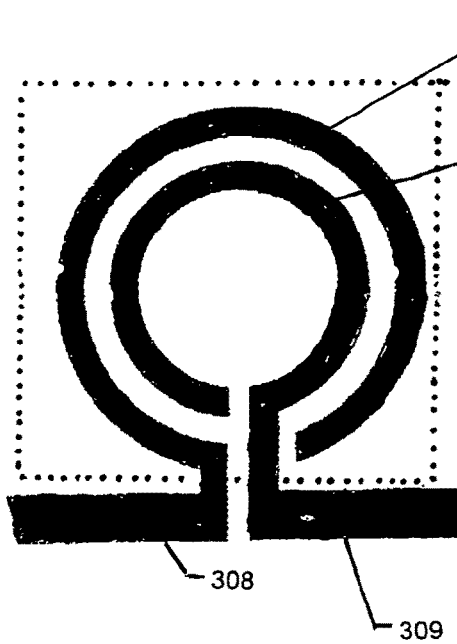
Figure 3C:
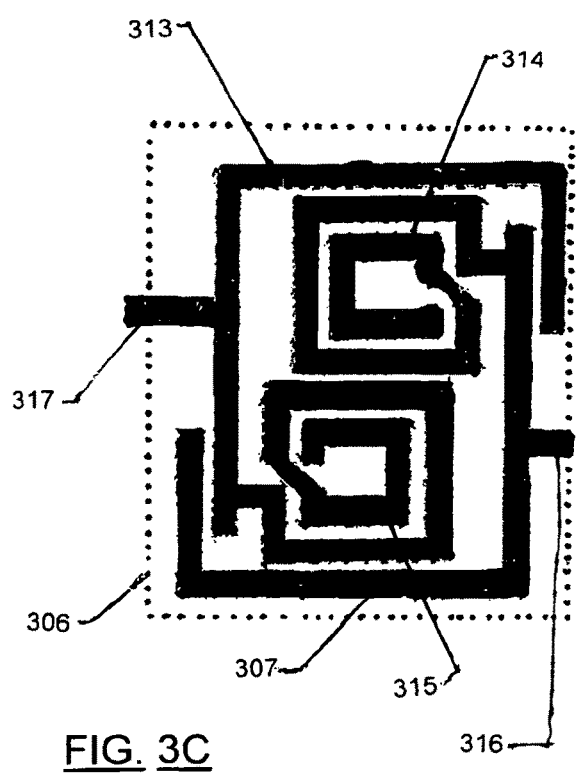

FIG. 3 depicts plan views of four exemplary SRF structures, each coupled with unbalanced stripline over a ground plane. FIG. 3A depicts the MRF comprised of an SRR structure with outer ring 301 and inner ring 302 created within an open area surrounded by backside ground plane. FIG. 3B depicts a plan view of an MRF comprised of two coupled spirals providing a negative impedance component as a series connection within an unbalanced stripline 308, 309. Spiral rings 312,312 are capacitively coupled. FIG. 3C depicts an MRF serially connected into an unbalanced stripline 316, 317. This MRF is comprised of coupled reverse spirals 314, 315 with additional capacitive coupling provided through wires 307,313. A window 306 is opened in the backside ground plane metallization film to enhance field-coupling into the material.

EXEMPLARY EMBODIMENTS

In each of the following exemplary embodiments, a differential signal is calculated in the interrogator for each sensing operation. Each sensing operation comprises a single frequency measurement of a source signal level and a response signal. The impedance calculator calculates a differential level based on the difference between the source signal level and the response signal level for each sensing operation. The impedance calculator processes differential signals to determine a component of the wave impedance of the material. In general, the spectrometer, calibrated with material of known permittivity and fixed interrogator positioning, can specify the material wave impedance. When the interrogator is not calibrated, the wave impedance can be monitored over a period of time, but not specified.

A First Embodiment

Figure 4:
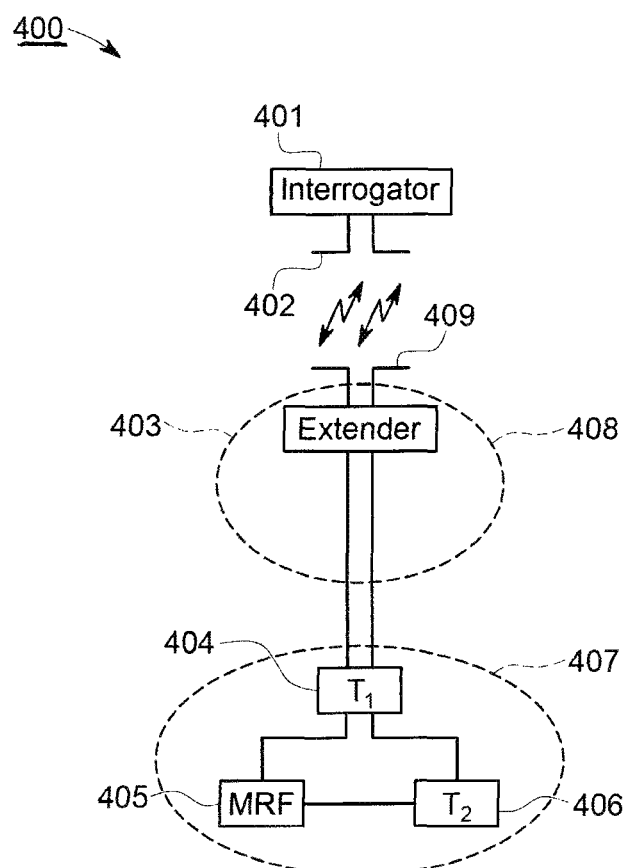
FIG. 4 depicts a first embodiment circuit configuration of the spectrometer in accordance with the present teachings.

FIG. 4 depicts a first exemplary embodiment circuit configuration of the spectrometer comprised of interrogator 401 including first antenna 402, range extender 403, and sensing structure 407. The sensing structure is comprised of a series connection of MRF 405, first transponder $T_1$ 404 and second transponder $T_2$ 406, all disposed within the material 407. Transponder $T_1$ is connected as a load termination for range extender 403. The interrogator provides an RF source of power to the transponders through the range extender.

The range extender comprises a broadband antenna 409 connected with a transmission line. The transmission line is at least partially disposed within an RF-opaque material 408. Bi-directional RF signals propagate through the range extender between antenna 409 and the sensing structure. These bi-directional signals propagating through the range extender are not attenuated by field-coupling to the RF-opaque material 408. The transmission line is typically a coaxial cable terminated with or without baluns or a balanced line. Two transponders $T_1$ and $T_2$ are disposed within the material 407.

In a sensing operation with the first embodiment, each transponder is enabled separately with an RF signal from the interrogator propagating through air to antenna 409 and further through the range extender. Each enabled transponder generates a backscatter signal which propagates through the range extender to the first antenna of the interrogator. The backscatter signal from transponder $T_1$ is measured by the interrogator to define a source signal level. The source signal level is not affected by the wave impedance of material 407. The backscatter signal from transponder $T_2$ is measured by the interrogator to define a response signal level. The response signal level is affected by the wave impedance of the material.

In a first sensing operation, a first differential level is calculated in the interrogator based on the difference between a first source signal level and a first response signal level. When the differential level is obtained at a frequency a few percent removed from the MRF resonant frequency, the first differential level is strongly effected by the imaginary part of the material permittivity and minimally effected by the real part of permittivity. In this embodiment, with sensing based only on a first sensing operation, the impedance calculator can specify or monitor the dielectric constant of the material.

In this first embodiment, with one or more of second sensing operations, RF source signals are acquired and measured by the interrogator in a manner similar to that of the first sensing operation. The interrogator calculates a differential level for each second sensing operation. The second differential levels typically are calculated for multiple RF frequencies.

Based on second sensing operations, the impedance calculator determines the MRF resonant frequency and calculates a resonant differential signal level for the MRF resonant frequency. This resonant differential signal level together with the first differential level are further processed by the impedance calculator to provide a unique value for the loss tangent of the material. In this embodiment, both the real and imaginary part of permittivity can be determined using sensing operations at multiple RF frequencies.

The impedance calculator in this embodiment can be calibrated with a single RF source power level and operated with multiple of power levels and interrogator-MRF physical separations. This can be accomplished wherein the system response is linear and signal levels are processed as logarithmic levels. This can be especially advantageous toward simplifying calibrations for applications wherein the interrogator is handheld portable or deployed as payload on a UAV drone.

In the first embodiment, controlled tuning of the sensing structure is not implemented.

A Second Embodiment

Figure 5:
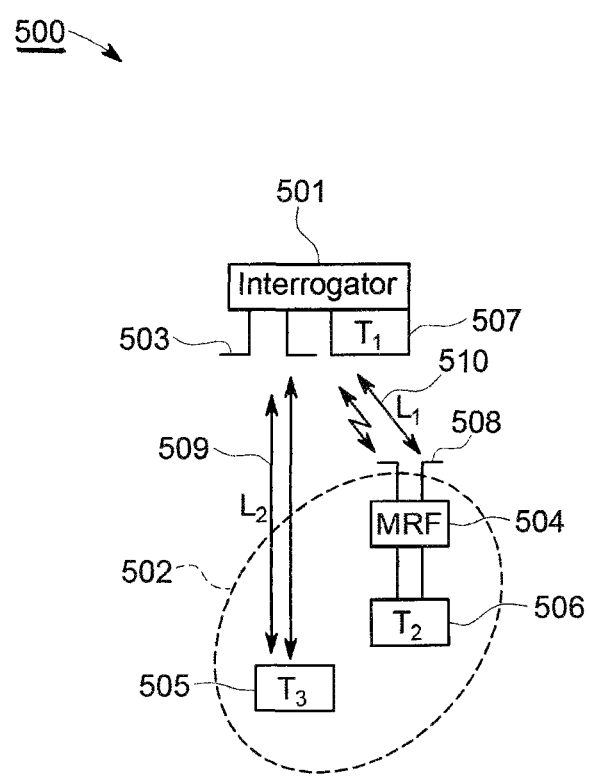
FIG. 5 depicts a second embodiment circuit configuration of the impedance spectrometer with in accordance with the present teachings.

FIG. 5 depicts a second exemplary embodiment circuit configuration of the impedance spectrometer comprised of two sensing structures. Interrogator 501 comprises antenna 503 to provide an RF source for enabling two transponders $T_2$ and $T_3$ disposed within material 502. Transponder $T_1$ is co-located with the interrogator. The RF source provided by the interrogator is coupled through antenna 503 to broadband antenna 508 over signal path of length $L_2$ 509. A portion of signal path $L_2$ extends through the material. Antenna 503 couples with transponder $T_3$ over a signal path $L_1$ 510. Signal path $L_1$ typically is provided external to material 502.

Within the first sensing structure, second antenna 508 is typically disposed proximal to and not coupled to material 502 and is connected to the MRF and transponder. The first sensing structure comprises MRF 504, transponder $T_2$ 506 and antenna 508 connected in series. A backscatter response signal is determined by MRF field-coupling to the material and controlled by transponder $T_2$. The MRF is configured as a two-terminal device wherein the filter return loss ratio $S_{11}$ is affected by field-coupling to the material. Transponder $T_2$ may comprise a standard 2-terminal RFID IC including types typically disposed within a passive RFID tag.

In a variation within the second embodiment, the first sensing structure may comprise MRF of FIG. 2B wherein the terminals 214 are connected to antenna 508.

In yet another variation within the second embodiment, the MRF of FIG. 2B is adapted wherein balanced line terminals 214 are shorted together without connection to antenna 508. In this configuration, the MRF provides a single component sensing structure providing field-coupling to the material, RF antenna, and transponder $T_2$.

In the second embodiment of FIG. 5, a second sensing structure is disclosed. The second sensing structure, comprising a third transponder $T_3$ 505, embedded within the material, provides a backscattered signal to the interrogator. The third transponder provides a passive or semi-passive RFID function responsive to the RF source from the interrogator. Transponder $T_3$ comprises a broadband antenna and is not responsive to local field-couplings with the material 502. provides a second field-coupling with the material and the first antenna 503. Transponder $T_3$ is disposed at sufficient distance into the material to provide an enhanced signal attenuation for backscattered signal propagating to the interrogator through the material. The backscattered signal level from transponder $T_3$ measured by interrogator 501 is minimally affected by the imaginary part of the material wave impedance and maximally effected by the RF attenuation with propagation through the material.

In a first sensing operation, a first source signal level is measured by the first transponder $T_1$ for RF signal transmitted from the interrogator. A first response signal level is generated by backscatter from the first sensing structure comprised of the series-connected MRF 504, transponder $T_2$ and antenna 508. The interrogator calculates a first differential level based on difference between the first source signal level and the first response signal level. The first sensing operation is obtained using an RF frequency sufficiently removed from the resonant frequency of MRF 504 wherein the first differential level uniquely defines the imaginary part X of the material wave impedance. In the first sensing operation, the first differential level is typically obtained using a single RF source signal frequency and is processed by the impedance calculator to specify or monitor the material dielectric constant.

In a second sensing operation involving transponder $T_3$, the backscatter signal received at the interrogator is measured to provide a second differential level. The is level is sensitive to the real part R of the material wave impedance and relatively independent of the imaginary component of the material wave impedance. The differential level thus obtained is strongly dependent on the separation length $L_2$. The loss tangent, based on calibrations, is calculated by the impedance calculator as the ratio R/X obtained by the first and second sensing operations.

It is noted that the second embodiment can be operated to provide the real part of wave impedance using the same second sensing operations as are disclosed with the first embodiment. This alternative protocol eliminates the need for transponder 505, but does require multiple sensing operations with multiple RF frequencies.

In this embodiment, the spectrometer is calibrated using fixed RF propagation path for backscattered response signal. Using only a first differential level and two transponders $T_1$ and $T_2$ with calibration, the impedance calculator can specify the dielectric constant of the material. Using either of the two disclosed sensing operation scenarios for sensitive to the real part of the material wave impedance, the loss tangent of the material is specified or monitored. In this exemplary second embodiment and its modification, controlled tuning of the sensing structure is not implemented.

A Third Embodiment

Figure 6:
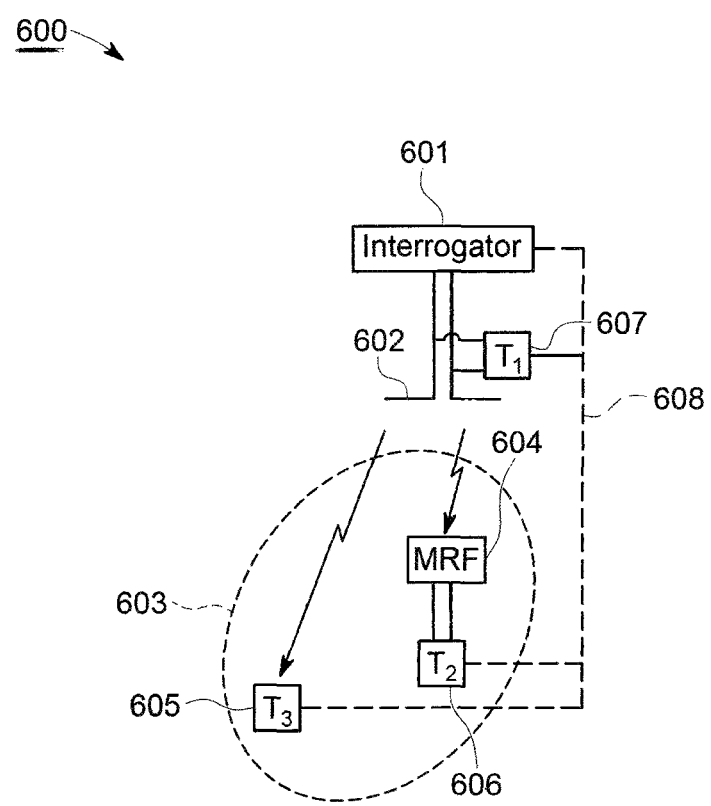
FIG. 6 depicts a third embodiment circuit configuration of the impedance spectrometer in accordance with the present teachings.

FIG. 6 depicts a third exemplary embodiment circuit configuration of the impedance spectrometer wherein interrogator 601 provides an RF source coupled through antenna 602 to first and second sensing structures embedded within the material 603. First transponder $T_1$, typically collocated with the interrogator, measures the source signal level. A first sensing structure comprises MRF 604 and transponder $T_2$ 606. A second sensing structure comprises transponder $T_3$. The sensing structures in FIG. 6 are depicted as embedded within the material, but in related configurations MRF 604 disposed proximal to and coupled with the material 603 but not imbedded within. The signal attenuation path between transponder $T_3$ and antenna 602 comprises sufficient length to enhance the effect of the real part of material wave impedance on the response signal level at transponder $T_3$. Signal levels are measured at each transponder and communicated to the interrogator via databus 608.

With the third embodiment, a first sensing operation comprises obtaining a differential level at a single RF frequency different from the MRF resonant frequency. A first source signal level is measured by the first transponder $T_1$ for RF signal transmitted from the interrogator and received at transponder $T_2$ and the MRF. A first response signal level is measured by transponder $T_2$. The interrogator calculates a first differential level based on difference between the first source signal level and the first response signal level. The first differential level uniquely defines the imaginary part X of the material wave impedance based on calibrations and measurements with fixed RF signal paths.

In a second sensing operation, a second source signal level is measured by the transponder $T_1$ and a second response signal level is measured by transponder $T_3$. The interrogator calculates a second differential level based on difference between the second source signal level and the second response level. The second differential level has enhanced sensitivity to the real part R of material wave impedance due to attenuation of RF signal sourced from the interrogator.

An alternative scenario for sensing the real part of material wave impedance is to use the same sensing operation disclosed for the first embodiment wherein multiple RF frequencies are used to determine a resonant response signal level at the resonant frequency of the MRF.

The impedance calculator specifies or monitors the wave impedance in all scenarios based on analysis of differential levels.

In this embodiment, a calibrated impedance calculator can specify both the real and imaginary components of the material wave impedance based on first and second differential levels. The third embodiment can specify the material wave impedance using a single RF frequency when configured with three transponders or using multiple RF frequencies when configured with two transponders.

Fourth Embodiment

A fourth embodiment is comprised of an interrogator and a single component sensing structure. In this embodiment, the sensing structure is comprised of an MRF alone, wherein the MRF is physically configured to provide field-coupling with the material, transponder communication function, and an antenna powered by RF from the interrogator. In this embodiment the MRF is field-coupled to the material of interest and is disposed within or proximal to the material. For example, the MRF of FIG. 2B, comprising an integral transponder IC 212 metamaterial split ring resonator SRR can be adapted to provide the fourth embodiment by shorting the outer ring at terminals 214. The resulting structure provides the MRF, a backscatter antenna and transponder $T_2$. Transponder $T_1$ co-located with the interrogator provides a measure of the source signal level. A response signal generated as back scatter by transponder $T_2$ is measured in the interrogator. In this embodiment, a differential signal based on the RF source and response signals is calculated by the impedance calculator. A first differential signal level, obtained with an RF frequency sufficiently removed from the MRF resonance frequency, is processed by the impedance calculator to specify or monitor the imaginary part of the material wave impedance. Second differential signals, obtained with sensing operations at multiple frequencies including the resonance frequency of the MRF, are processed by the impedance calculator to determine a resonance differential level at the resonant frequency of the MRF. The resonance differential level together with the first differential level are used by the impedance calculator to calculate the real part R of the material wave impedance and the loss tangent δ=X/R based on calibrations. This fourth embodiment spectrometer provides a minimum physical configuration having advantages of further miniaturization and reduced cost.

Tuned Sensor Structure Embodiments

Figure 7:
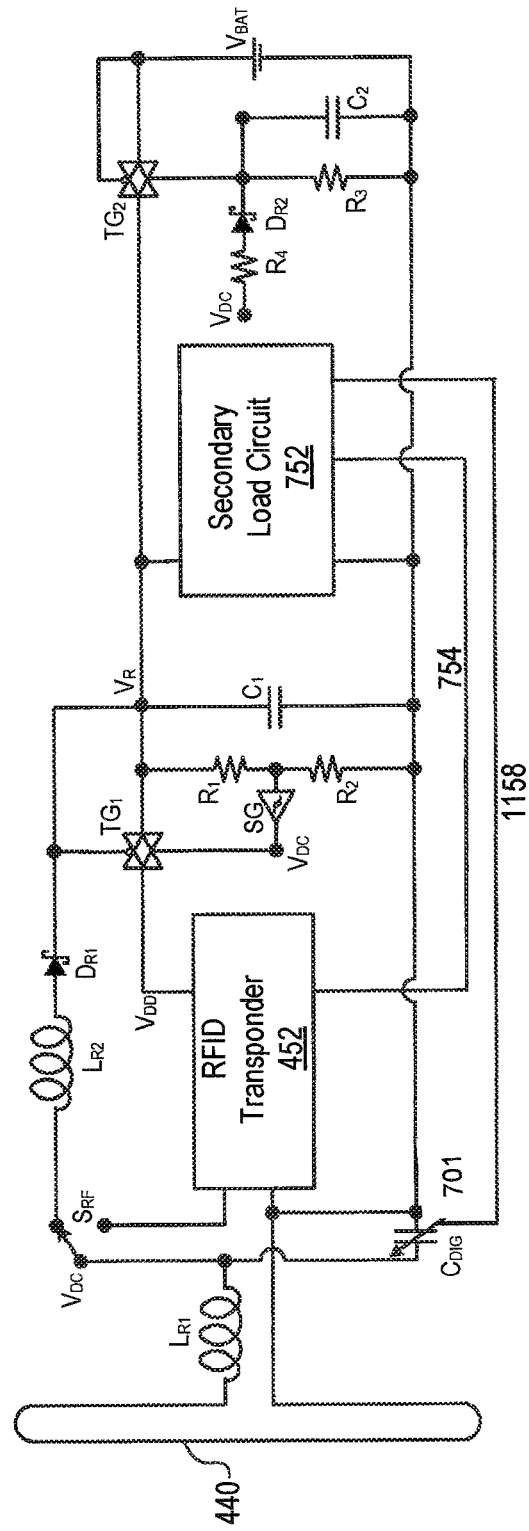
FIG. 7 depicts a prior art semi-passive transponder circuit with programmable antenna tuning and powered with harvested RF (U.S. Patent Application 2017/0237466).

FIG. 7 is a prior art semi-passive transponder circuit wherein its resonant antenna 440 is self-tuned by an integral programmed capacitance $C_{DIG}$ 701. In embodiments, this circuit can provide the function of transponder $T_3$ 505 within the sensor structure of the second embodiment communicating directly with the first antenna of the interrogator. The transponder of FIG. 7 is comprised of RF energy harvesting circuitry having a resonant voltage multiplication circuit for charging a local battery $V_{BAT}$. When battery voltage is low, the RF harvesting circuit provides transponder operation by charging a small capacitor providing short term energy. Transponder operation is not interrupted with low battery voltage wherein the transponder continues to operate with RF energy harvested. The integral antenna 440 provides for RF harvesting and an RFID tag function. This circuit comprises a circuit which disconnects the battery power supply when battery voltage $V_{BAT}$ drops below a threshold level. The antenna 440 is tuned by the transponder internal circuitry under program control from the interrogator. Antenna 440 is capacitively tuned by varactor diode $C_{DIG}$ 701 with bias control voltage supplied through wire 1158. Other transponder circuitry includes a generic RFID transponder IC 452, the antenna, an impedance-matching network, an RF switch $S_{RF}$, inductor and diode components for resonant RF-to-DC voltage multiplication.

In another embodiment, the semi-passive transponder circuit of FIG. 7 is modified and used as transponder $T_2$ in the embodiment of FIGS. 4 and 5. For this embodiment, the circuit of FIG. 7 is used with antenna 440 removed. The varactor $C_{DIG}$ 701 is connected to provide a tuning capacitance within the resonant TRE of FIG. 7. The impedance of the series connected MRF, TRE and transponder $T_2$ determine the backscatter response level in this embodiment.

Figure 1B:
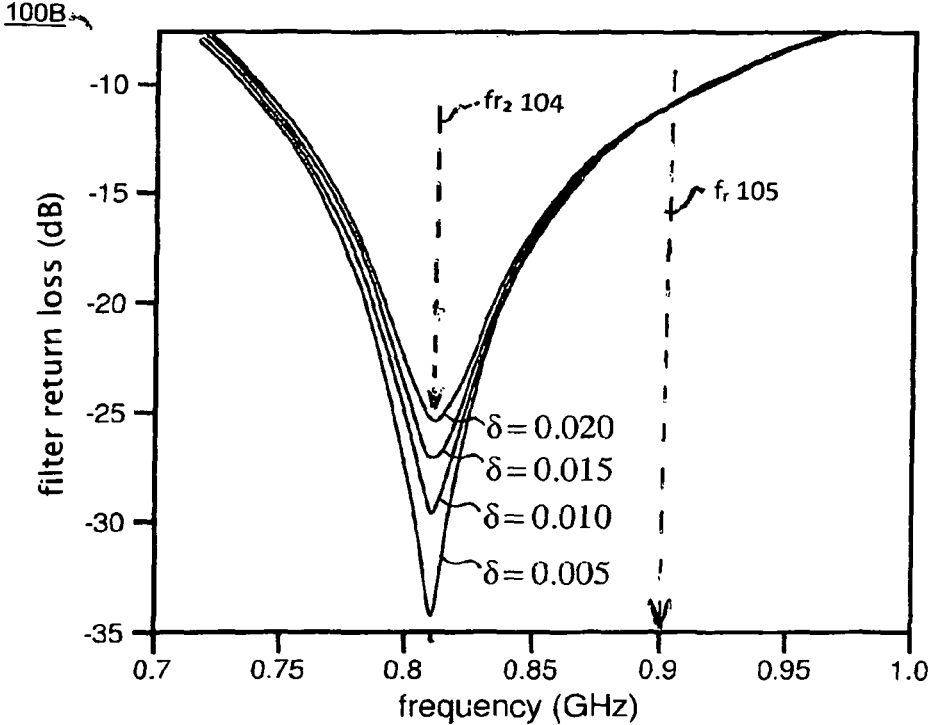

The cross-correlation response of the TRE and the MRF in series connection provides the desired response sensitivity to the imaginary part of wave impedance when the TRE is tuned to frequency $f_{r1}$ 103 (ref. FIGS. 1A and 1B). In similar fashion, the cross-correlation response obtained at frequency $f_{r2}$ 104 provides the desired responsivity to the real part of wave impedance. In this embodiment, tuning of the TRE is controlled by the interrogator and communicated to transponder $T_2$ by wireless means.

APPLICATION CONFIGURATIONS

The spectrometer physically configured and operated to provide the wave impedance of a material in several environments. In an embodiment, the wave impedance of agricultural materials including earth soil is monitored. Soil moisture effects the dielectric constant and soil salinity effects the loss tangent of of the soil wave impedance. The first and second exemplary embodiment can be physically configured for this environment.

The spectrometer can sense the bulk impedance of agricultural product, in raw or processed form, comprised of one or more materials selected from a group comprised of maize, cocoa, coffee, wheat, barley, tea, nuts, peanuts, tree oils, timber, and silage. Each of the three exemplary embodiments can be physically configured for this environment.

The spectrometer can sense the bulk impedance of a processed liquid comprised of one or more of beer, wine, rum, and industrial chemicals. The first exemplary embodiment can be physically configured for sensing liquids in bottled or cask environments. The third exemplary embodiment is suitable for this environment.

The spectrometer can sense the bulk impedance of cement at various stages in a curing process. For example, the dielectric constant of Portland cement changes as the cement cures at a construction or highway paving site. Cement at a construction site or as road pavement can be monitored during a short curing process or over an extended time period. A sensing structure comprised of the MRF/$T_2$ components can be permanently embedded within cement in certain projects.

The spectrometer can provide a means for determination of the frozen or unfrozen content of a material wherein the wave impedance of the material is different for frozen and thawed physical states. The first and second exemplary embodiments configured and operated for monitoring dielectric constant only are are especially suited for this application environment.

Figure 8A:
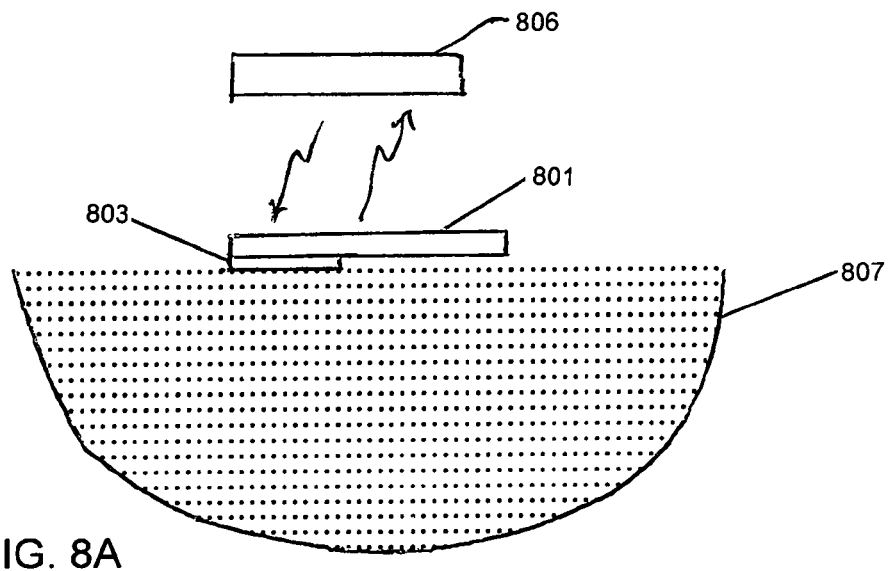
FIGS. 8A and 8B depict a perspective view of the impedance spectrometer with wireless control disposed in a noninvasive surface location.
Figure 8B:
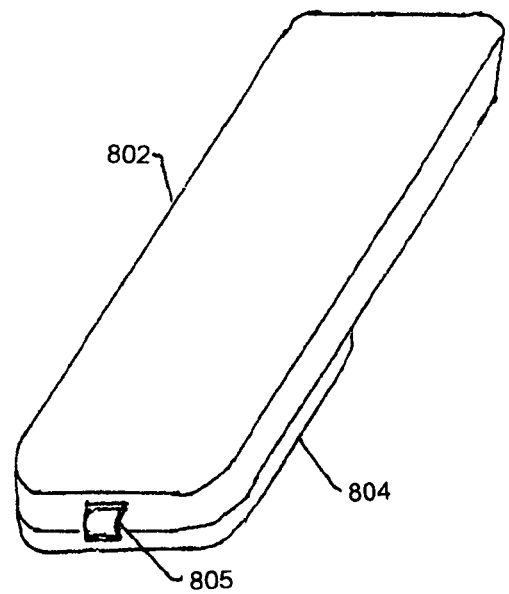

FIG. 8A depicts a sectioned view of the impedance spectrometer with wireless control disposed in a noninvasive surface location. In this embodiment a mobile phone 801 communicates as a node within cellular network 806. The spectrometer 803 is connected with the mobile phone 801 and is disposed at the surface of material 807. FIG. 8B is a perspective view of the mobile phone 802 and spectrometer 804 connected through USB port and cable 805. This physical configuration based on the third exemplary embodiment is useful for noninvasive monitoring of material wave impedance.

Figure 9:
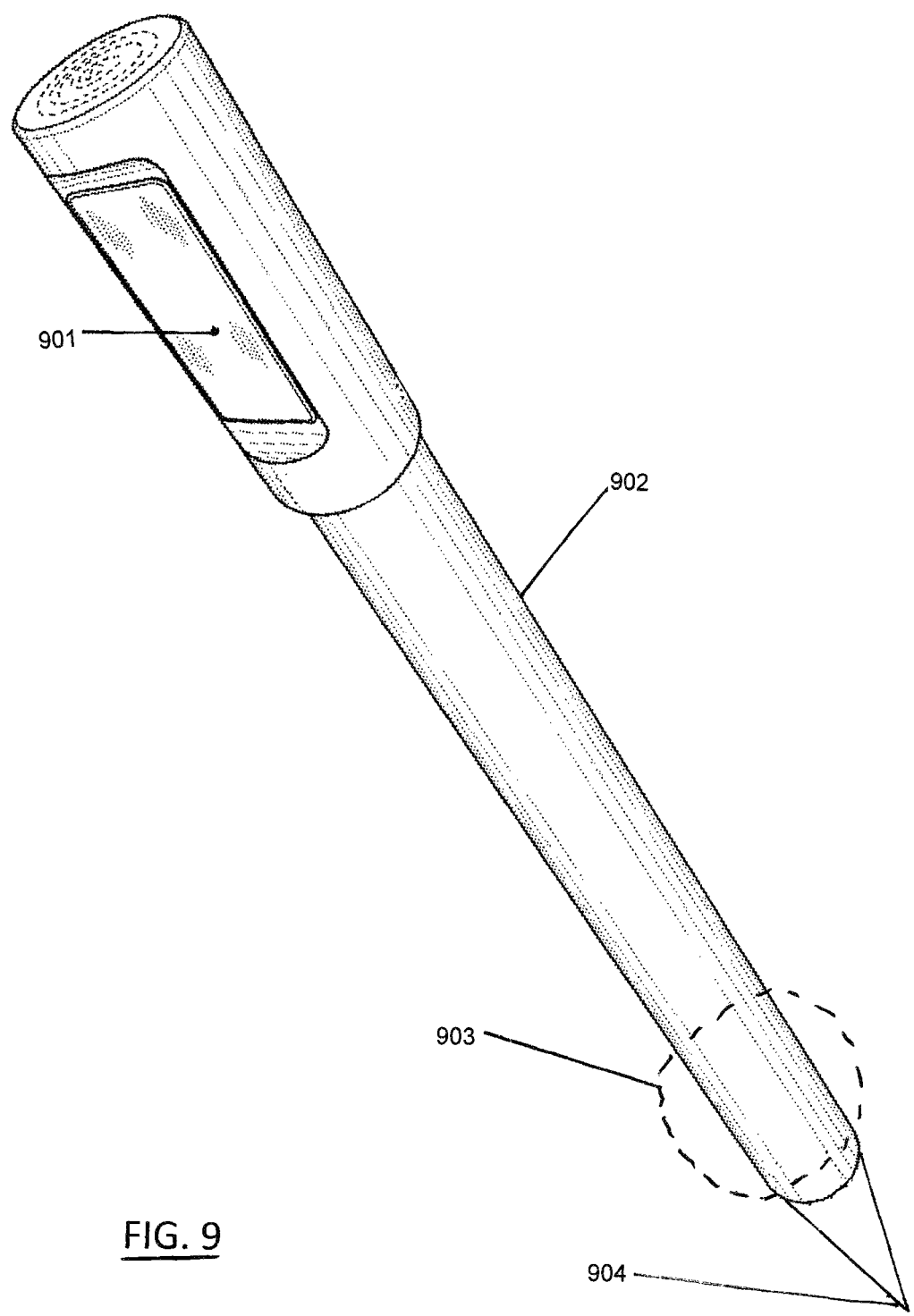
FIG. 9 depicts a perspective view of the impedance spectrometer configured as a cylinder for insertion into a material.

FIG. 9 depicts a perspective view of the impedance spectrometer configured as a cylinder 902 with a tip 904 structured for insertion into a material. The sensing structure 903 is disposed near the tip. Communication with a mobile phone 901 is provided by databus. This physical configuration, based on the third exemplary embodiment, provides a portable spectrometer suitable for sensing into wet soil, piles of ag and food product, and material disposed beyond RF-opaque media.

Figure 10:
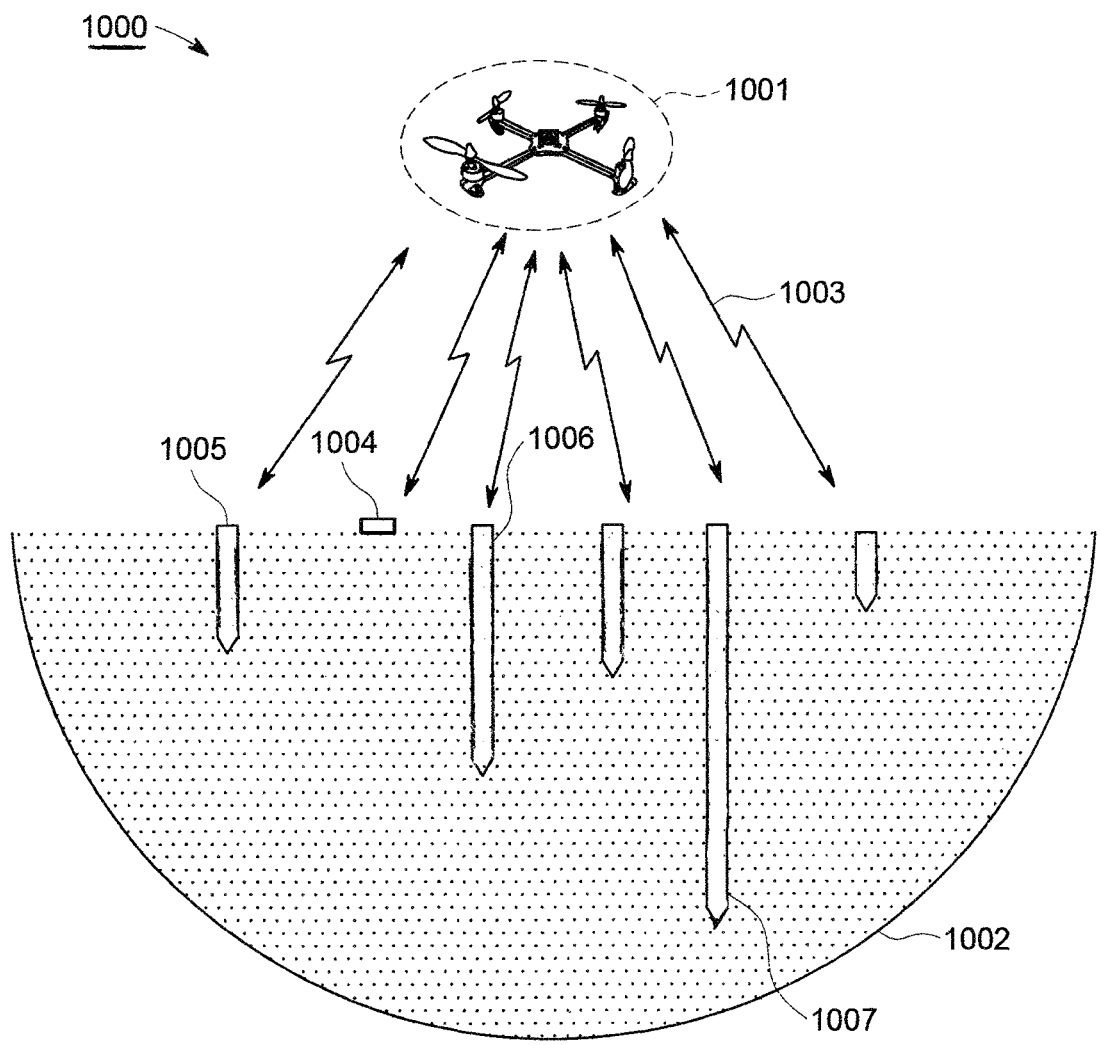
FIG. 10 depicts a perspective of the impedance spectrometer configured with the interrogator as payload on a UAV drone and with multiple sensing structures buried in an agricultural field or building structure.

FIG. 10 depicts a perspective of the impedance spectrometer configured with the interrogator 1001 as payload on a UAV drone and with multiple sensing structures buried in an agricultural field or building structure. RF power and signaling is accomplished through wireless link 1003. The sensing structures 1005, 1006, 1007 configured within plastic pipe cylinders are suitable for sensing at differing depths within a material and with implementations based on the first exemplary embodiment. The second exemplary embodiment is suitable for disposing the spectrometer 1004 noninvasively at the surface of the material. The range extender in this environment may extend into the material for distances in excess of 5 meters, typically limited by the practical length of the cylindrical pipe enclosing the range extender.

It is understood that although the disclosure teaches many examples of embodiments in accordance with the present teachings, many additional variations of the invention can easily be devised by those skilled in the art after reading this disclosure. Various modifications may be made without deviating from the spirit and scope of the invention. As a consequence, the scope of the present invention is to be determined by the following claims.

The invention claimed is:

1. An impedance spectrometer for sensing a wave impedance of a material, the impedance spectrometer comprising an interrogator adapted for controlling and processing RF signals communicating with a sensing structure, the sensing structure further comprising:
a first transponder, wherein the first transponder generates a source analog signal responding to an RF control signal communicated from the interrogator by wired or wireless operative coupling;
a metamaterial resonant filter (MRF) receiving the source analog signal from the first transponder and generating a response analog signal affected by MRF coupling into the material, wherein the MRF coupling comprises at least one of an electric, electromagnetic, or magnetic field, and the MRF is operational with at least one of negative permittivity or negative permeability within the MRF;
a second transponder, receiving the response analog signal from the MRF, wherein the level of the response analog signal is communicated to the interrogator via RF signals through a wired or wireless operative coupling, and the interrogator is further comprised of:
an impedance calculator, wherein the impedance calculator determines the real part and/or the imaginary part of the wave impedance of the material based on one or more sensing operations, wherein each sensing operation provides a measure of the difference in signal levels between the source analog signal and the response signal level at a controlled frequency.

2. The impedance spectrometer of claim 1 wherein the MRF comprises one or more of a split ring resonator (SRR), coupled spiral resonator, fractile metamaterial and variations thereof.

3. The impedance spectrometer of claim 1 wherein at least a portion of the operative coupling between the interrogator and one or more transponders is a wired connection provided by a digital bus.

4. The impedance spectrometer of claim 1 wherein at least a portion of the operative coupling between the interrogator and one or more transponders comprises wireless RFID technology, wherein the transponders are active or semi-passive transponders.

5. The spectrometer of claim 1 wherein at least a portion of the operative coupling is comprised of a wired coupling through RF-blocking material between the controller and the transponders.

6. The impedance spectrometer of claim 1 wherein the operative coupling is implemented at an RF signal frequency different from that of the RF signal providing field coupling within the MRF.

7. The impedance spectrometer of claim 1 wherein the operative coupling between the interrogator and one or more of the transponders is based on wireless RFID technology wherein the transponders comprise passive RFID tags.

8. The impedance spectrometer of claim 1 wherein one or more of the transponders is powered by an RF energy harvester receiving RF energy by wireless means from the interrogator or other external RF power source.

9. The impedance spectrometer of claim 1 wherein the integrator and the transponders are disposed on the same physical circuit platform.

10. The impedance spectrometer of claim 1 wherein the interrogator is carried as payload on an unmanned aerial vehicle (drone).

11. The impedance spectrometer of claim 1 wherein the interrogator is disposed within a wand stick structure.

12. The impedance spectrometer of claim 1 wherein the interrogator is connected with or disposed within a mobile phone.

13. The spectrometer of claim 1 wherein the material is earth soil having the wave impedance affected by moisture and ionic conduction.

14. The spectrometer of claim 1 wherein the material comprises an agricultural product, in raw or processed form, further comprised of one or more materials selected from a group comprised of maize, cocoa, coffee, wheat, barley, tea, nuts, peanuts, tree oils, timber, bales of hay, and silage.

15. The spectrometer of claim 1 wherein the material comprises a processed food product further comprising a water or alcohol component.

16. The spectrometer of claim 1 wherein the material is comprised of an alcohol or water component, further comprising one or more of beer, wine, rum, and industrial chemicals.

17. The spectrometer of claim 1 wherein the material comprises curing cement, wherein the wave impedance of the cement changes with time as the cement cures.

18. The spectrometer of claim 1 wherein the material is a material in a frozen or unfrozen state, and the wave impedance of the material is different for its frozen and unfrozen states.

19. A method for sensing a wave impedance of a material, the method comprising:
  performing one or more sensing operations controlled by a controller, wherein each sensing operation comprises transmitting a first analog signal from a first transponder into a metamaterial resonant filter (MRF) and the MRF transmitting a second analog signal into a second transponder in response to the first analog signal, wherein each sensing operation determines a signal level for the first and second analog signals and the signals within each sensing operation have the same frequency;
  generation of a coupling by the MRF into the material, the coupling comprising at least one of an electric, electromagnetic, or magnetic field, wherein said coupling into the material affects the electrical impedance of the MRF;
  calculating, by the controller, a difference level for the first and second analog signals for each sensing operation;
  calculating the real part of the wave impedance of the material based on the difference level obtained for the one or more sensing operations wherein the real part of the wave impedance of the material is uniquely related to the resonant frequency of the MRF;
  calculating the imaginary part of the wave impedance of the material based on multiple sensing operations obtained over a frequency range that encompasses the resonance frequency of the affected MRF, wherein the imaginary part of the wave impedance is uniquely related to the difference level at the MRF resonance frequency.

20. The method of claim 19 wherein the impedance calculator is calibrated by operating the impedance spectrometer in specific environments with material of known wave impedance.

* * * * *